United States Patent [19]
Menzel et al.

[11] Patent Number: 5,639,735
[45] Date of Patent: Jun. 17, 1997

[54] ANTITUMOR ANTIBIOTIC COMPOUNDS: HAYUMICINS AND ANALOGS THEREOF

[75] Inventors: Rolf Menzel, Princeton Junction; Scott T. Taylor, West Windsor, both of N.J.; Mitsuaki Tsunakawa, Middletown, Conn.; Keiichi Numata, Wallingford, Conn.; Tamotsu Furumai, Middletown, Conn.

[73] Assignee: Bristol-Myers Squibb Company, Princeton, N.J.

[21] Appl. No.: 308,232

[22] Filed: Sep. 19, 1994

[51] Int. Cl.$^6$ .......................... A61K 31/71; A61K 31/70; C07H 17/04; C12P 19/60
[52] U.S. Cl. .................. 514/33; 435/78; 514/34; 536/4.1; 536/6.4; 536/16.8; 536/16.9; 536/17.2
[58] Field of Search ................. 435/78; 536/6.9, 536/4.1, 16.8, 16.9, 17.2, 6.4; 514/33, 24

[56] References Cited

U.S. PATENT DOCUMENTS 4,572,895  2/1986  Masataka et al. .

FOREIGN PATENT DOCUMENTS 6-32796   of 1994   Japan .
6-228185  of 1994   Japan .

OTHER PUBLICATIONS

C.A. 121:132270q vol. 121 #11 (Sep. 12, 1994) Uchida Et Al ABS of "Tennen Yuki Kabobotsu" 1993 35th 258–65.
C.A. 121:81107g vol. 121 No. 7 Aug. 15, 1994 ABS of JP0632296 Published Feb. 8, 1994.

Uchida, et al., "Chrymutasins: Novel–Aglycone Antitumor Antibiotics from a Mutant of *Streptomyces chartreusis*. I. Taxonomy, Mutation, Fermentation, Isolation and Biological Activities", The Journal of Antibiotics, vol. 47, No. 6, Jun. 1994, pp. 648–654.

Uchida, et al., "Chrymutasins: Novel–Aglycone Antitumor Antibiotics from a Mutant of *Streptomyces chartreusis*. II. Characterization and Structural Elucidation", The Journal of Antibiotics, vol. 47, No. 6, Jun., 1994, pp. 655–667.

Uchida, et al., "Chrymutasins: a New Type of Aglycone Related to Chartreusin; Novel Antitumour Antibiotics from a Mutant of *Streptomyces chartreusis*", J. Chem. Soc., Chem. Commun., No. 3, Feb. 7, 1994, pp. 323–324.

Uchida, et al., "A Novel Compound Related to Chartreusin from a Mutant of *Streptomyces chartreusis*", The Journal of Antibiotics, vol. 46, No. 10, Oct., 1993, pp. 1611–1615.

Uchida et al., Tennen Yuki Kagobutsu Toronkai Koen Yoshishu, 35th, 258–265 (1993) (complete article).

*Primary Examiner*—Herbert J. Lilling
*Attorney, Agent, or Firm*—Suzanne E. Babajko

[57] ABSTRACT

Hayumicin compounds, obtainable by cultivation of a strain of Actinomadura sp. designated ATCC 55432, and analogs of these compounds. The novel compounds have antitumor as well as antibiotic, particularly antibacterial, activity.

5 Claims, 13 Drawing Sheets

ANTITUMOR ANTIBIOTIC COMPOUNDS: HAYUMICINS AND ANALOGS THEREOF

FIELD OF THE INVENTION

The present invention relates to novel antitumor antibiotics which may be obtained by cultivation of a strain of Actinomadura sp., to ether, ester and/or amide analogs of these compounds, and to salts and prodrugs thereof. The present invention also relates to methods of preparing, compositions containing and methods of using the inventive compounds, and to the novel strain of Actinomadura sp.

SUMMARY OF THE INVENTION

Cultivation of a strain of the microorganism Actinomadura sp., which has been deposited with the American Type Culture Collection as ATCC 55432, yields the novel compounds hereinafter referred to as Hayumicin A, B, $C_1$, $C_2$ and D. These compounds have been found to possess antibiotic activity, particularly in inhibiting the growth of bacteria (especially gram positive bacteria), as well as antitumor activity. Analogs of these compounds, described herein, are also expected to exhibit the aforementioned antitumor antibiotic activities.

The present invention provides the novel compounds of the following formula I:

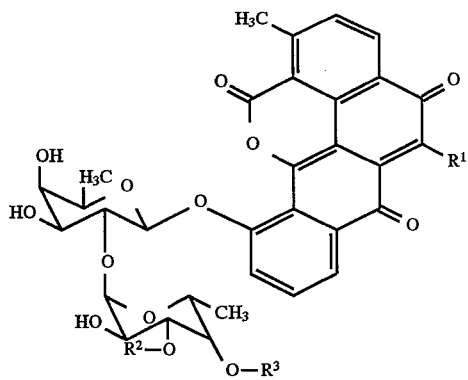

where
$R^1$ is -OH or -NH$_2$;
$R^2$ is hydrogen or alkyl (preferably, methyl); and
$R^3$ is hydrogen or alkyl (preferably, methyl); ethers, esters and/or amides of said compound; and salts thereof.

Hayumicin A has the following structure:

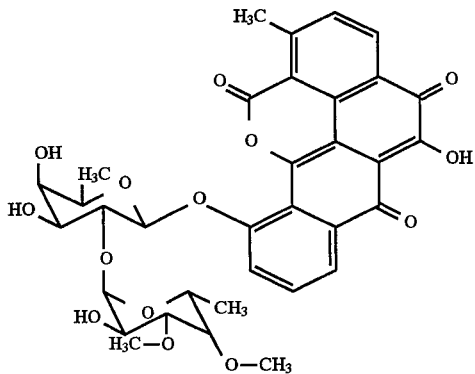

corresponding to the name 10-[[6-deoxy-2-O-(6-deoxy-3,4-di-O-methyl-α-D-galactopyranosyl)-β-D-galactopyranosyl]oxy]-5-hydroxy-1-methyl-4H-benzo[h]naphtho[8,1,2-cde][1]benzopyran-4,6,12-trione.

Hayumicin B has the following structure:

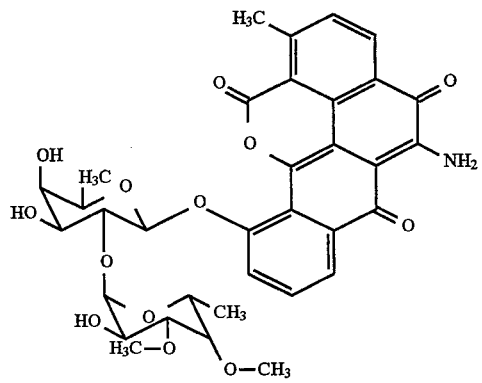

corresponding to the name 5-amino-10-[[6-deoxy-2-O-(6-deoxy-3,4-di-O-methyl-α-D-galactopyranosyl)-β-D-galactopyranosyl]oxy]-1-methyl-4H-benzo[h]naphtho[8,1,2-cde][1]benzopyran-4,6,12-trione.

Hayumicin $C_1$ has the following structure:

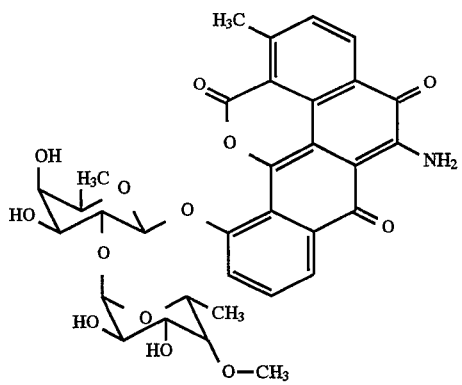

corresponding to the name 5-amino-10-[[6-deoxy-2-O-(6-deoxy-4-O-methyl-α-D-galactopyranosyl)-β-D-galactopyranosyl]oxy]-1-methyl-4H-benzo[h]naphtho[8,1,2-cde][1]benzopyran-4,6,12-trione.

Hayumicin $C_2$ has the following structure:

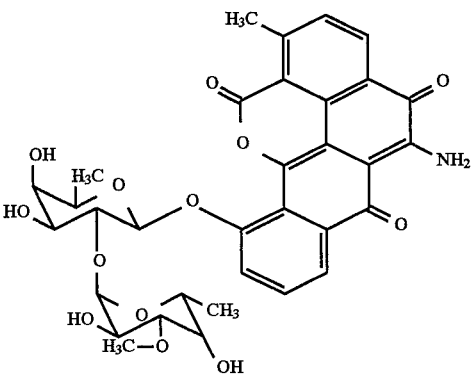

corresponding to the name B-amino-10-[[6-deoxy-2-O-(6-deoxy-3-O-methyl-α-D-galactopyranosyl)-β-D-galactopyranosyl]oxy]-1-methyl-4H-benzo[h]naphtho[8,1,2-cde][1]benzopyran-4,6,12-trione.

Hayumicin D has the following structure:

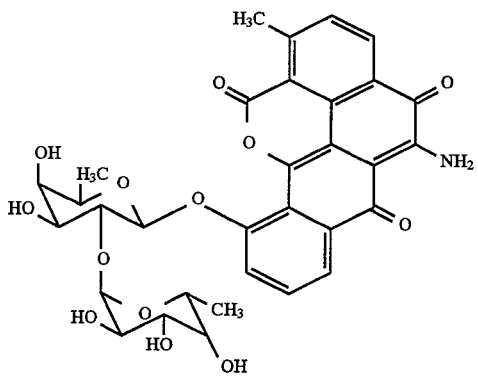

corresponding to the name 5-amino-10-[[6-deoxy-2-O-(6-deoxy-α-D-galactopyranosyl)-β-D-galactopyranosyl]oxy]-1-methyl-4H-benzo[h]naphtho[8,1,2-cde][1]benzopyran-4,6,12-trione.

The present invention therefore provides the compounds of the formula I, ethers, esters and/or amides of these compounds, and salts thereof. Prodrugs of these compounds are also contemplated. Thus, unless otherwise indicated, the term "inventive compounds", as used herein, includes the compounds of the formula I, ethers, esters and/or amides of these compounds, as well as salts and prodrugs thereof. It is also understood that all stereoisomers of the inventive compounds are contemplated herein, whether alone (that is, substantially free of other isomers), in a mixture of certain stereoisomers (for example, as a racemate) or in any other mixture thereof.

The present invention also provides novel compositions comprising, and methods of using, the inventive compounds as antitumor and antibiotic (particularly, antibacterial) agents. For example, the inventive compounds may be used to prevent or treat tumors or bacterial infections in animals, particularly humans, or as disinfectants for suppressing bacterial growth on surfaces such as those of surgical instruments. Methods of making the inventive compounds, and the novel strain of Actinomadura sp. described herein, are further provided.

DETAILED DESCRIPTION OF THE INVENTION

Figure 1:
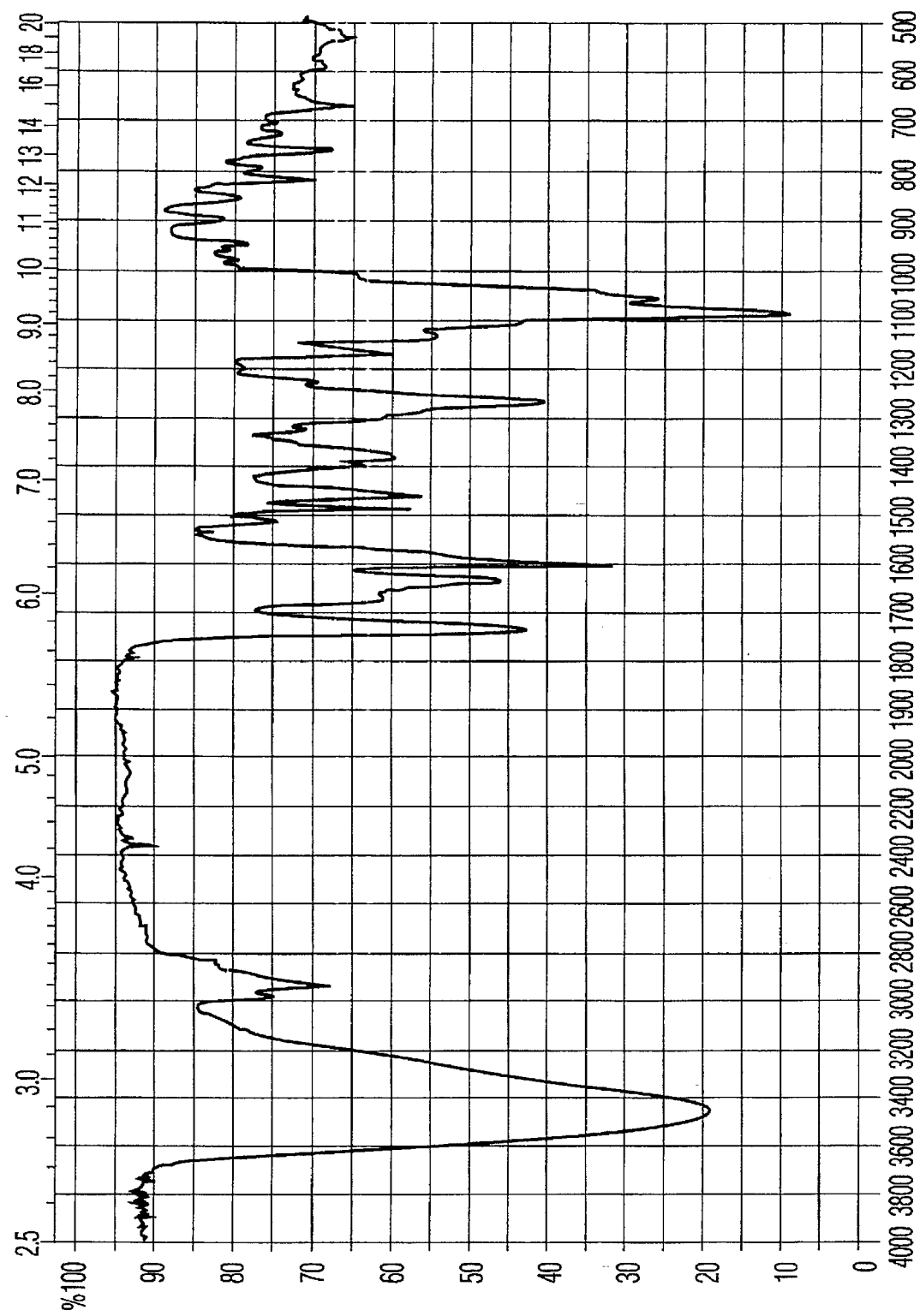
FIG. 1 shows the infrared (IR) spectrum of Hayumicin A in KBr.
Figure 2:
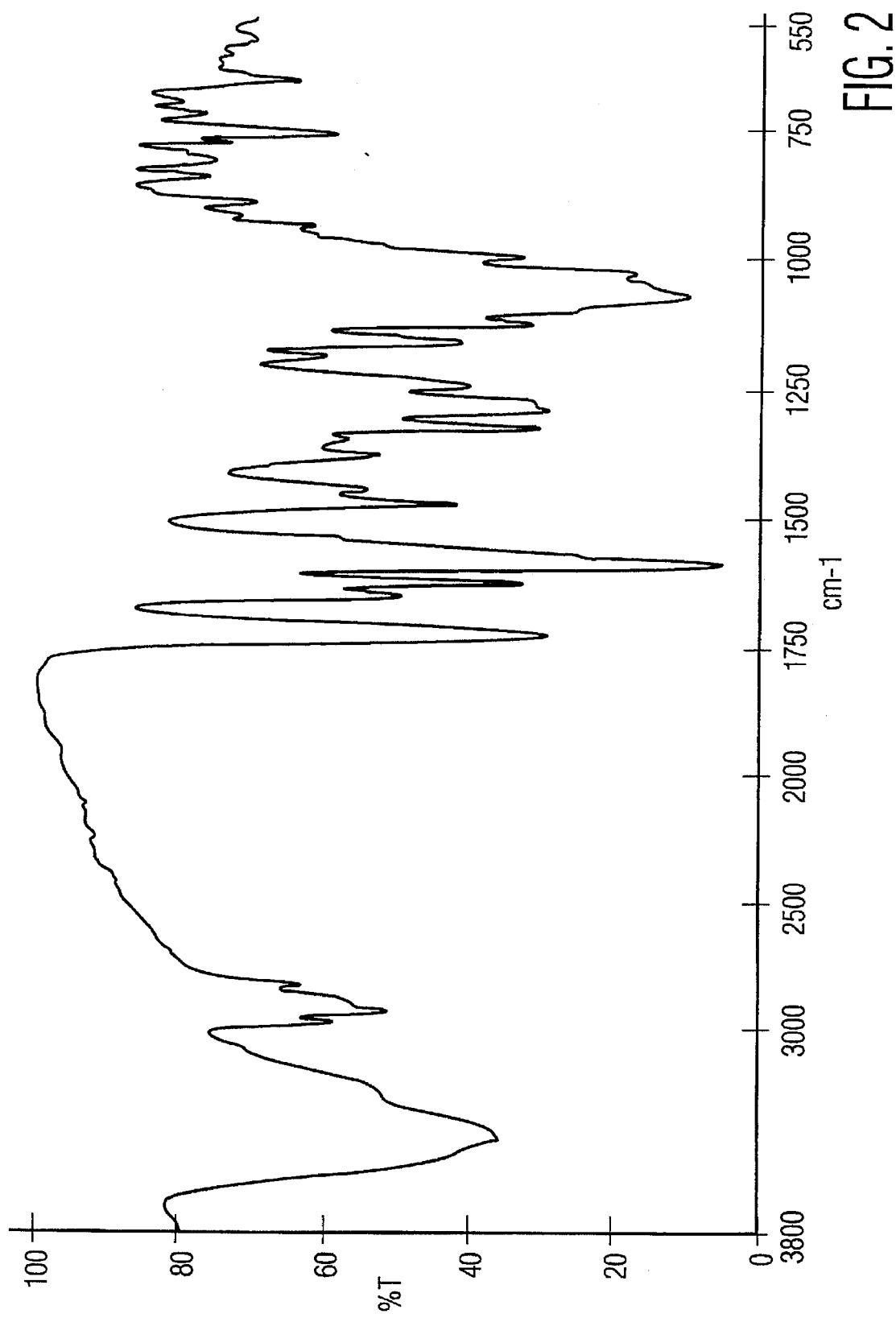
FIG. 2 shows the infrared (IR) spectrum of Hayumicin B in KBr.
Figure 3:
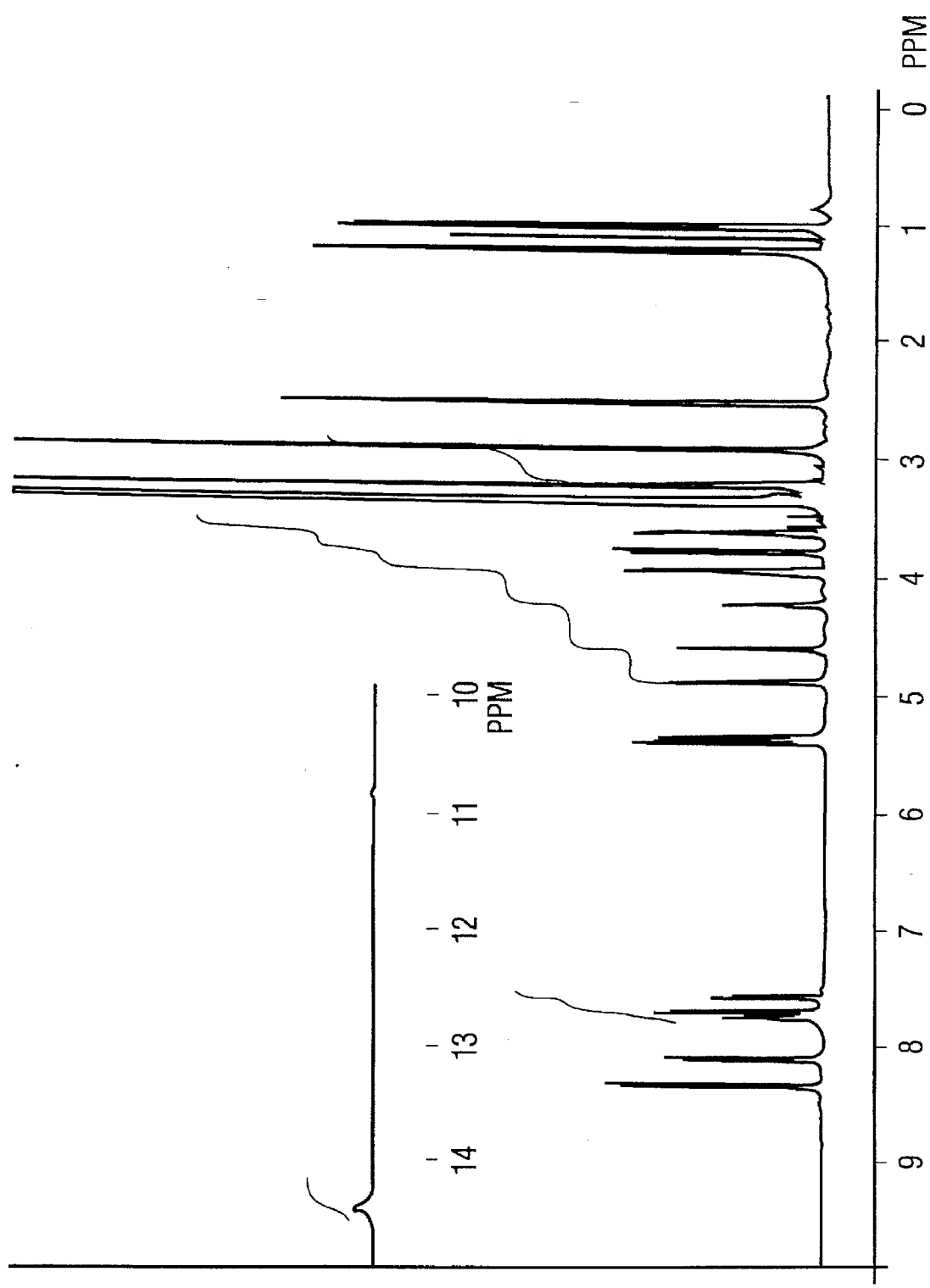
FIG. 3 shows the $^1$H NMR spectrum of Hayumicin A in dimethylsulfoxide (DMSO-$d_6$), 400 MHz.
Figure 4:
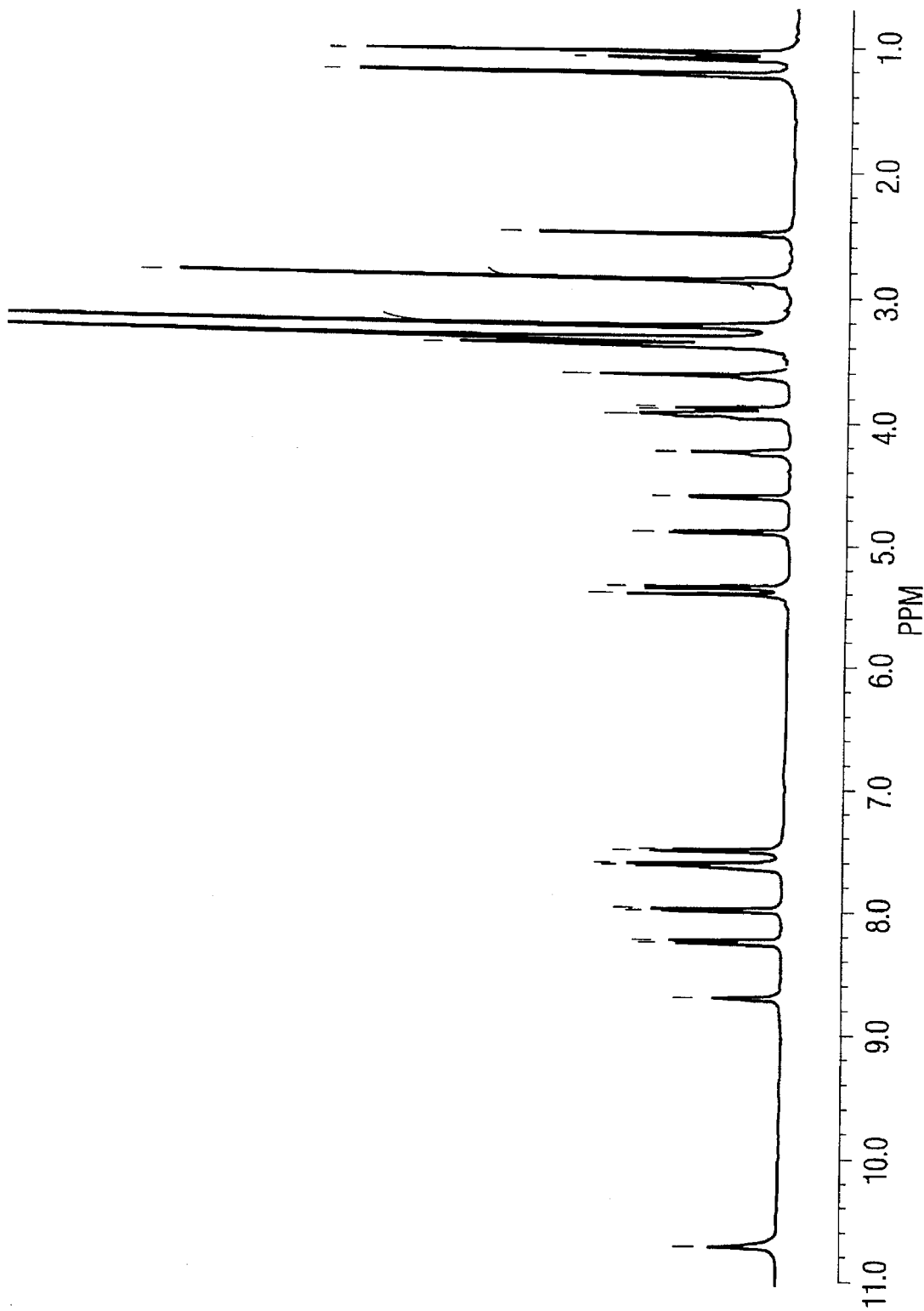
FIG. 4 shows the $^1$H NMR spectrum of Hayumicin B in dimethylsulfoxide (DMSO-$d_6$), 500 MHz.
Figure 5:
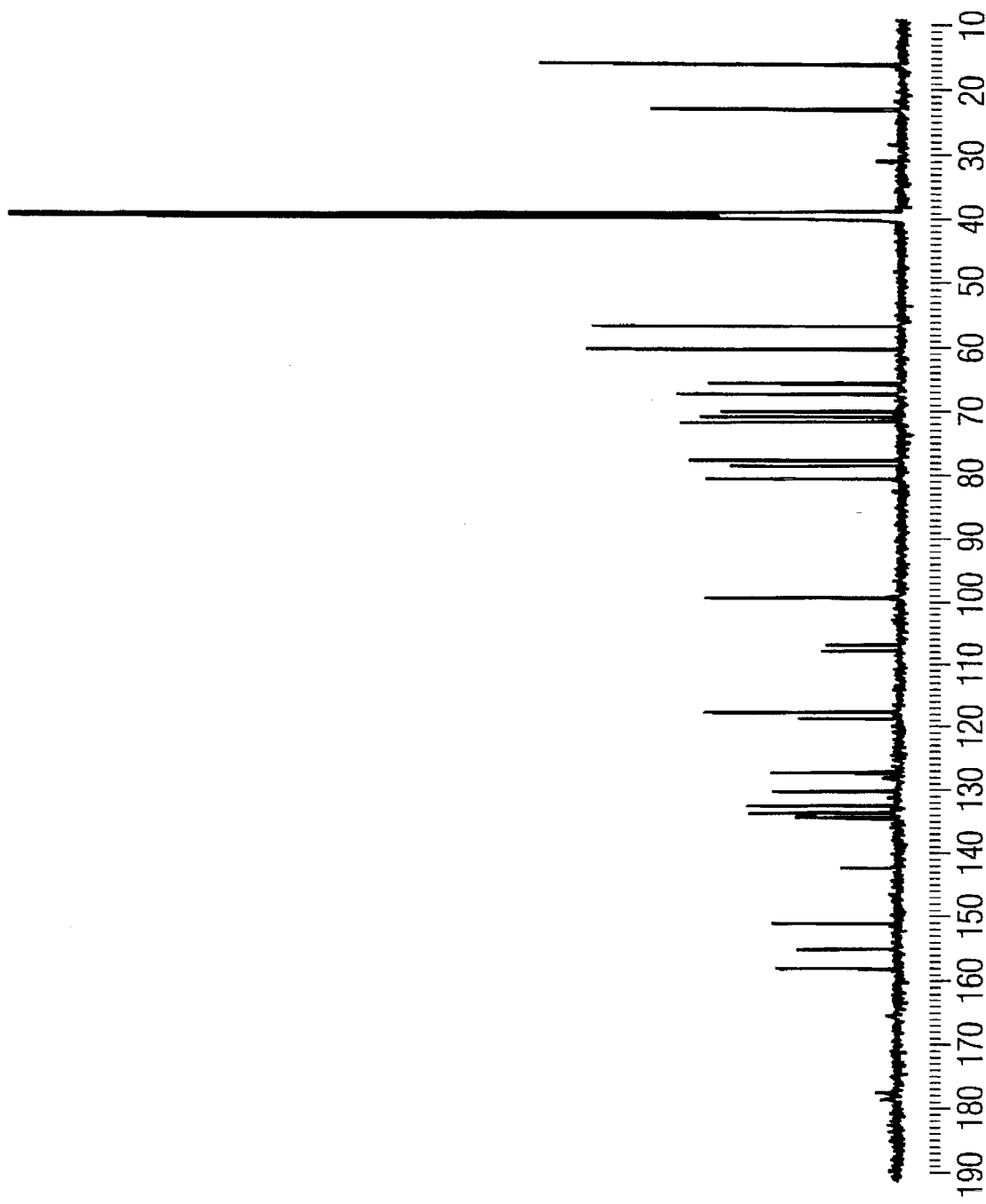
FIG. 5 shows the $^{13}$C NMR spectrum of Hayumicin A in dimethylsulfoxide (DMSO-$d_6$), 100 MHz.
Figure 6:
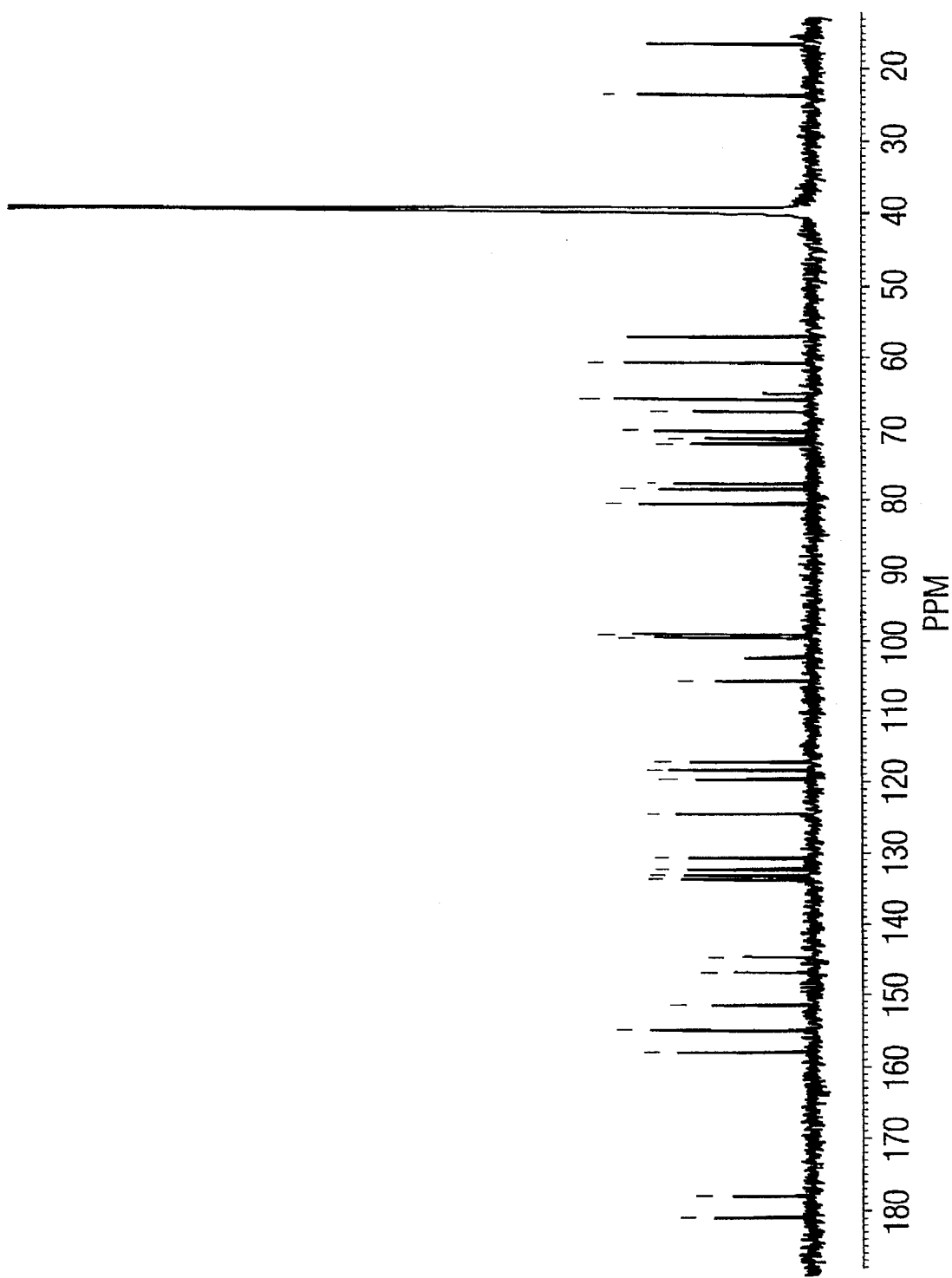
FIG. 6 shows the $^{13}$C NMR spectrum of Hayumicin B in dimethylsulfoxide (DMSO-$d_6$), 125 MHz.

The present invention is described further as follows.

The Microorganism

The microorganism which may be used for the production of Hayumicins A, B, $C_1$, $C_2$ and D is Actinomadura sp., a strain of which was isolated from a soil sample obtained in Nagasaki, Japan. A subculture of this microorganism may be obtained from the permanent collection of the American Type Culture Collection, 12301 Parklawn Drive, Rockville, Md. 20852, where it was deposited on May 20, 1993 and received the accession number ATCC 55432. In addition to the specific microorganism described herein, it is understood that mutants, such as those produced by the use of chemical or physical mutagens including X-rays, etc., and microorganisms whose genetic makeup has been modified by molecular biology techniques, may also be cultivated to produce the aforementioned Hayumicin compounds.

Isolation of the microorganism Actinomadura sp. ATCC 55432 from a soil sample in which it is present may be accomplished by first suspending the soil sample in a sterile diluent, such as buffered saline containing 0.01% gelatin, and shaking vigorously. A dilution of this suspension may then be plated onto a nutrient medium. The composition of an exemplary such medium is:

|  | % By Wgt |
| --- | --- |
| Soluble starch | 0.1 |
| Glucose | 0.25 |
| NZ-case | 0.015 |
| Yeast extract | 0.01 |
| Fish meal extract | 0.025 |
| $CaCO_3$ | 0.015 |
| Agar | 2.0 |
| Water | Added to 1 liter |

This medium may be adjusted to pH 7.0 and sterilized at 121° C. for 15 minutes prior to use.

After 7–10 days incubation at 28° C., colonies of Actinomadura sp. may be removed ("picked off") and placed onto yeast extract-malt extract agar (ISP-2) slants.

The morphological properties of the strain of Actinomadura sp. of the present invention were determined after incubation for 2 to 4 weeks at 28° C. according to the methods described by Shirling and Gottlieb (E. B. Shirling and D. Gottlieb, "Methods for characterization of Streptomyces species", Intern. J. Syst. Bact., 16:313–340 (1966)). The cultural and physiological characteristics were determined by the methods of these same authors, and also by those described by Waksman (S. A. Waksman, "The Actinomycetes, Vol. II. Classification, identification and description of genera and species, pp. 328–334, The Williams & Wilkins Co., Baltimore (1961)). The Manual of Color Names (Japan Color Enterprise Co., Ltd. (1987)) was used to designate the colors observed in the cultural studies of this microorganism.

As a result of these studies, the microorganism has been found to have the following characteristics:

(1) Morphology

Vegetative mycelia do not fragment on agar or in liquid media. Mature aerial mycelia are generally powdery and tinted white to light purple. Straight chains of more than 10 spores were observed at the tips of sporulating aerial mycelia. The spores were elliptical in shape with a warty or knobby surface and measured 0.3–0.5×0.7–1.0 mm. They were not motile.

(2) Cultural characteristics

Actinomadura sp. ATCC 55432 formed good vegetative growth on organic media. The color of the vegetative mycelia ranged from deep purple to dark purple on yeast extract-malt extract agar and glycerol asparagine agar. Dark-purple to dull-purple diffusable pigments were also produced in these media. The diffusible pigments acted as pH indicators, becoming pale-purple upon addition of 0.1N NaOH. The macroscopic cultural properties of Actinomadura sp. ATCC 55432 on various agar media are summarized in the following Table 1.

TABLE 1

Cultural Characteristics of Actinomadura sp. ATCC 55432

| Medium | Vegetative Mycelium | Reverse Side | Aerial Mycelium | Diffusible Pigment |
|---|---|---|---|---|
| Sucrose-nitrate agar (Waksman medium No. 1) | Colorless | Colorless | White (389) | Light purple (348) |
| Glucose asparagine agar (Waksman medium No. 2) | Colorless | Colorless | None | Bright bluish purple (350) |
| Yeast extract-malt extract agar (ISP No. 2) | Dark purple (371) | Dark purple (371) | Purplish white (396) | Dark purple (372) |
| Oatmeal agar (ISP No. 3) | Colorless | Colorless | Purplish white (396) | None |
| Inorganic salts-starch agar (ISP No. 4) | Colorless | Colorless | Purplish white (396) | None |
| Glycerol asparagine agar (ISP No. 5) | Deep purple (366) | Dull purple (370) | Light purple grey (405) | Dull purple (370) |
| Tyrosine agar (ISP No. 7) | Colorless | Colorless | None | None |
| Nutrient agar (Waksman medium No. 14) | Colorless | Colorless | None | None |
| Bennett's agar (Waksman medium No. 30) | Dark purple (371) | Colorless | Purplish white (396) | Dark purple (372) |

(3) Physiological traits and carbon utilization

The physiological traits and carbon utilization pattern of Actinomadura sp. ATCC 55432 are shown in the following Tables 2 and 3, respectively.

TABLE 2

Physiological Characteristics of Actinomadura sp. ATCC 55432

| TEST | RESULTS |
|---|---|
| Starch hydrolysis (on ISP med. No. 4) | Negative |
| Nitrate reduction (Difco, nitrate broth) | Negative |
| Milk (Difco, 10% skimmed milk) | |
| Coagulation | Negative |
| Peptonization | Positive |
| Cellulose decomposition (sucrose nitrate solution with a paper strip as the sole carbon source) | Negative |
| Gelatin liquefaction | |
| On plain gelatin | Positive |
| On glucose peptone gelatin | Negative |
| Melanin formation (On ISP med. No 7) | Negative |
| Temperature range for growth (°C.) | 15–45 |
| Optimum temperature (°C.) (on yeast starch agar) | 29–40 |
| pH range for growth | 5–8 |
| Optimum pH (in trypticase soy broth, BBL) | 6–7 |
| Growth in/at | |
| Lysozyme | |
| 0.01% | Positive |
| 0.1% | Negative |
| NaCl | |
| 2.0% | Positive |
| 8.0% | Negative |

TABLE 3

Utilization of carbon sources by Actinomadura sp. ATCC 55432

| Carbon Source | Growth |
|---|---|
| D-Glucose | + |
| L-Arabinose | − |
| D-Xylose | − |
| Inositol | + |
| Mannitol | + |
| D-Fructose | − |
| L-Rhamnose | + |
| Sucrose | + |
| Raffinose | − |

− = Negative
+ = Positive
(ISP medium No. 9, 37° C. for 21 days)

(4) Cell chemistry

Whole cell analysis, carried out by the method described by Lechevalier and Lechevalier (H. A. Lechevalier and M. P. Lechevalier, "A critical evaluation of the genera of aerobic actinomycetes. *The Actinomycetales*" (H. Prauser, ed.), pp. 393–495, Jena, Gustav Fisher Verlag (1970)), and modified by Staneck and Roberts (J. L. Staneck and G. D. Roberts, "Simplified approach to identification of aerobic actinomycetes by thin-layer chromatography", *Appl. Microbiol.*, 28:226–231 (1974)), detected meso-diaminopimelic acid in the hydrolysates of whole cells; the LL isomer was not found. The hydrolysate also contained glucose, galactose, mannose and madurose. The menaquinone composition (determined according to the method of Collins et al. (M. C. Collins, H. N. Shah and D. E. Minnikin, "A note on the separation of natural mixtures of bacterial menaquinones using reverse-phase thin-layer chromatography", *J. Appl.*

*Bacteriol.*, 48:277–282 (1980)) was found to be 66% MK-9 (H6), 16% MK-9(H8), 3% MK-9(H2) and 3% MK-9(H10). Fatty acid analysis by the technique of Suzuki and Komagata (K. Suzuki and K. Komagata, "Taxonomic significance of cellular fatty acid composition in some Coryneform bacteria, *Int. J. Syst. Bacteriol.*, 33:188–200 (1983)) revealed the presence of 29.2% of 10-methyloctadecanoic acid (10-Meth 18:0), 26.4% of hexadecanoic acid (16:0), 17.2% of cis-9-octadecanoic acid and 10.8% of 2-hydroxy hexadecanoic acid.

The characteristics described above are in agreement with the generic description of Actinomadura given by Kroppensted, Stackenbrandt and Goodfellow (R. N. Kroppenstedt, E. Stackenbrandt and M. Goodfellow, "Taxonomic revision of the actinomycetes genera Actinomadurae and Microtetraspora", System. *Appl. Microbiol.*, 13:148–160 (1990)), and therefore serve to identify the microorganism as a species of the genus Actinomadura.

The present invention provides the above novel strain of Actinomadura sp. designated by ATCC 55432, which may be isolated from soil such as by the cultivation and isolation methods described herein. Also provided are microorganisms which have the identifying characteristics of the strain designated by ATCC 55432 as discussed above, and which are capable of producing Hayumicins A, B, $C_1$, $C_2$ and/or D. Such microorganisms include those originally designated as Actinomadura sp. ATCC 55432 which have been modified by physical, chemical, or biological means. Substantially pure, especially biologically pure, cultures of the microorganisms described herein are preferred.

The Novel Compounds

The novel compounds Hayumicins A, B, $C_1$, $C_2$ and/or D may be produced by fermentation of Actinomadura sp. ATCC 55432, or by any microorganism which is capable of producing said compounds, especially one also having the identifying characteristics of the aforementioned Actinomadura sp., and isolating one or more of said compounds from the fermentation broth. Cultivation under controlled conditions such as those described following is preferred for the preparation of these compounds. The aforementioned Hayumicin compounds are preferably produced by cultivation (fermentation) of Actinomadura sp. ATCC 55432 at or about a temperature of 25° C. to 38° C., preferably at 32° C., at a pH value ranging from 6 to 8, preferably at pH 7, under submerged aerobic conditions in an aqueous nutrient medium containing assimilable carbon (e.g., glucose, glycerol, fructose, sucrose, starch or other carbohydrates) and nitrogen (e.g., soybean meal, cotton seed meal, peptone, Corn steep liquor or yeast extract) sources.

The fermentation may be carried out until substantial antibiotic activity is imparted to the medium, usually about 96 to 144 hours. The fermentation, as well as subsequent isolation steps, may be monitored such as by means of a conventional paper disc, agar diffusion assay, e.g., with *Micrococcus luteus* ATCC 9341 as the assay organism. In addition, thin layer chromatographic analysis, followed by bioautography on, e.g., *M. luteus* may be used to follow the fermentation and subsequent isolation of the active materials of this invention.

The aforementioned Hayumicin compounds may be isolated and purified by means of art-recognized techniques from the fermentation broth. Preferably, upon completion of the fermentation, the whole broth is mixed with a water immiscible solvent, for example, an alcohol such as n-butanol, and the suspension stirred. The organic phase may be removed and concentrated in vacuo to dryness. The resulting residue may then be dissolved in a methanol:water mixture (7:3), and purified further by column chromatographies, such as on Diaion HP-20, silica gel and finally on Sephadex LH-20, to provide the pure compounds.

The term "salts", as used herein, denotes acidic and/or basic salts, formed with inorganic or organic acids and/or bases. While pharmaceutically acceptable salts are preferred, particularly when employing the compounds of the invention as medicaments, other salts find utility, for example, in processing these compounds, or where non-medicament-type uses are contemplated. Salts of these compounds may be prepared by art-recognized techniques, such as those employed in or analogous to the Examples herein.

The term "prodrugs", as used herein, denotes compounds which, in vivo, undergo chemical conversion to compounds of the formula I, ethers, esters and/or amides of these compounds, or salts thereof. Prodrug compounds may be prepared by art-recognized techniques such as those described in *Design of Prodrugs*, edited by H. Bundgaard (Elsevier, 1985).

The term "ester", as used herein, denotes a compound wherein the ester group -O-C(O)-Org is found in place of one or more hydroxyl groups of a compound of the formula I, preferably in place of a hydroxyl group at $R^1$. The term "Org", as used herein, denotes a monovalent organic moiety bonded through a carbon atom, and preferably denotes an alkyl or aryl group. Esters may be prepared from compounds of the formula I by art-recognized techniques, such as those employed in or analogous to the Examples herein.

The term "amide", as used herein, denotes a compound wherein the amide group -NH-C(O)-Org or the amide group -N(Org)-C(O)-Org is found in place of the amino group at $R^1$ of a compound of the formula I. Each group "Org" is independently defined as above. Amides may be prepared from compounds of the formula I by art-recognized techniques, such as those employed in or analogous to the Examples herein.

The term "ether", as used herein, denotes a compound wherein the ether group -O-Org is found in place of one or more hydroxyl groups of a compound of the formula I, preferably in place of a hydroxyl group at $R^1$. "Org" is as defined above, with the proviso that, when $R^1$ is -$NH_2$, the "Org" moiety of any ether group present is alkyl or aryl. Ethers may be prepared from compounds of the formula I by art-recognized techniques, such as those employed in or analogous to the Examples herein.

Compounds of the invention may contain, as appropriate, one or more of the aforementioned ether, ester and/or amide groups.

The term "alkyl", as used herein, denotes open-chain branched or unbranched hydrocarbon groups, preferably having 1–12 carbons in the normal chain, which may be unsubstituted or substituted by appropriate substituents such as one or more hydroxyl, aryl, amino, alkylamino, dialkylamino, carboxyl, or alkyloxycarbonyl groups. Exemplary unsubstituted such groups include methyl, ethyl, propyl, butyl, pentyl, and hexyl.

The term "aryl", as used herein, denotes carbocyclic aromatic groups containing 1 or 2 rings and 6 to 12 ring carbons, which may be unsubstituted or substituted by appropriate substituents such as one or more hydroxyl, alkyl, amino, alkylamino, dialkylamino, carboxyl, or alkyloxycarbonyl groups. Exemplary unsubstituted such groups include phenyl, biphenyl, and naphthyl.

Utility

It is preferred that the inventive compounds have a degree of purity such that they are suitable for use as an antitumor and/or antibiotic agent. A particularly preferred embodiment of the present invention provides a compound of the invention in its pure or substantially pure state. The pure or substantially pure compounds are preferably employed in preparing compositions such as those of the present invention. Further, the pure or substantially pure compounds, alone or as used in compositions exemplified by those described herein, are preferably employed in the methods of the present invention. It is understood that a single, or two or more, compound(s) of the present invention may be employed in any of the compositions or methods described herein.

The inventive compounds are useful as antimicrobial agents, having utility in inhibiting the growth of, including killing, microorganisms. The inventive compounds are particularly useful as antibacterial agents, particularly against gram-positive bacteria such as those of the genera Streptococcus (e.g., *Streptococcus pneumoniae, Streptococcus pyogenes* and *Streptococcus agalactiae*), Staphylococcus (e.g., *Staphylococcus aureus*), Micrococcus (e.g., *Micrococcus luteus*), Bacillus (e.g., *Bacillus subtilis*), and Escherichia (e.g., *Escherichia coli*). Thus, the compounds of the present invention may be employed in utilities suitable for such antimicrobial agents.

The inventive compounds may, for example, be used in a method for treating a host infected with a bacterium, or in preventing infection of said host by said bacterium, comprising the step of administering to the host a compound of the formula I, an ether, ester and/or amide or a physiologically tolerated salt or prodrug thereof in an amount effective for said prevention or treatment. Treatment of such infections according to the present invention includes both mitigation as well as elimination thereof.

Hosts administered the inventive compounds may be plants or animals, particularly animals such as dogs, cats and other domestic mammals and, especially humans. The dosage form and mode of administration, as well as the dosage amount, may be selected by one of ordinary skill in the art. The dosage amount will vary with the severity of the infection, and with the size and species of the host. Daily dosages for an adult human may be determined by methods known to one of ordinary skill in the art. Administration to a mammalian host may, for example, be oral, topical, rectal or parenteral. Administration to a plant host may be accomplished by, for example, application to seed, foliage or other plant part, or to the soil.

Compositions are also provided by the present invention which comprise a compound of the formula I, an ether, ester and/or amide, or a physiologically tolerated salt or prodrug thereof in an amount effective for the prevention or treatment of infection by a bacterium, and a physiologically tolerated vehicle or diluent. The term "physiologically tolerated" is equivalent to the term "pharmaceutically acceptable" when used in reference to the treatment of a mammalian host. The appropriate solid or liquid vehicle or diluent may be selected, and the compositions prepared, by methods known to one of ordinary skill in the art. Prevention or treatment of simultaneous infections by more than one bacterium is, of course, contemplated.

The inventive compounds may also be employed as antimicrobial agents useful in inhibiting the growth of, including killing, microorganisms present on a surface or in a medium outside a living host. The present invention therefore provides a method for inhibiting the growth of at least one bacterium present on a surface or in a medium, comprising the step of contacting the surface or medium with a compound of the formula I, an ether, ester and/or amide, or a salt thereof in an amount effective for the inhibition. Thus, the inventive compounds may be employed, for example, as disinfectants for surface treatments, such as disinfection of surgical instruments, or as preservatives for a variety of solid and liquid media susceptible to microbial growth. Suitable amounts of the inventive compounds may be determined by methods known to one of ordinary skill in the art. Compositions comprising a compound of the formula I, an ether, ester and/or amide, or a salt thereof in an amount effective for inhibiting the growth of at least one bacterium, and a vehicle or diluent, are also provided by the present invention.

The inventive compounds are further useful as antitumor agents. Thus, the present invention provides a method for preventing or treating a tumor, comprising the step of administering to a host a compound of the formula I, an ether, ester and/or amide, or a physiologically tolerated salt or prodrug thereof in an amount effective for such prevention or treatment. The present invention includes maintaining or reducing the size, as well as the elimination of, the tumor. The inventive compounds may be used to prevent or treat tumors susceptible to the compounds of the present invention. Compositions containing the inventive compounds are provided, comprising a compound of the formula I, an ether, ester and/or amide, or a physiologically tolerated salt or prodrug thereof in an amount effective for the prevention or treatment of a tumor, and a physiologically tolerated vehicle or diluent.

Hosts, dosages, modes of administration, etc., described above for the treatment of a host infected with a microorganism, apply to the use of the present compounds as antitumor agents, and those descriptions are incorporated herein.

Those of the inventive compounds with a higher cytotoxicity, especially Hayumicin B, are preferred for use as antitumor agents. Those of the inventive compounds with a lower cytotoxicity are preferred for use as antibiotics. When employed as antibiotics, the more cytoxic compounds are preferably administered topically.

The following examples further illustrate the invention, and are not intended to in any way limit the present claims. The examples demonstrate, inter alia, that compounds of the invention possess activity against a variety of microorganisms, particularly against gram positive bacteria.

EXAMPLE 1

Preparation of Hayumicin A and Hayumicin B (A) Fermentation of Actinomadura SO. ATCC 55432

A culture of Actinomadura sp. ATCC 55432 was maintained on yeast extract-malt extract agar (ISP-2). To prepare stock cultures for fermentation use, agar slants were inoculated and incubated at 28° C. for days. The composition of the agar slant medium was:

|  | % By Wgt |
|---|---|
| Soluble starch | 0.5 |
| Glucose | 0.5 |
| Meat extract | 0.1 |
| Yeast extract | 0.1 |
| NZ case | 1.6 |
| Agar | 1.5 |
| Water | to 100 |

The medium was sterilized at 121° C. for 20 minutes prior to use.

At the end of the incubation period, a portion of the mature slant was used to inoculate 100 mL portions of medium contained in 500 mL Erlenmeyer flasks. The medium had the following composition:

|  | % By Wgt |
| --- | --- |
| Soluble starch | 2.0 |
| Glucose | 0.5 |
| NZ case | 1.6 |
| Yeast extract | 0.2 |
| Fish meal D30X* | 0.5 |
| $CaCO_3$ | 0.3 |
| Water | to 100 |

*Banyu Nutrient Ltd.

At harvest, the growth was centrifuged at 3000 rpm for 15 minutes at 4° C. The pellet so obtained was resuspended in a half volume of 20% aqueous glycerol, and 0.3 mL aliquots of the suspension were distributed into sterile vials for subsequent use as stock cultures.

When needed, 0.3 mL of the stock culture (maintained in frozen form) was thawed and used to inoculate 100 mL of the liquid medium described above, again contained in 500 mL Erlenmeyer flasks. The inoculated flasks were incubated on a rotary shaker at 32° C. for 4 days. This constituted the seed fermentation. After the 4 day incubation period, 5 mL of this seed culture were used to inoculate 100 mL of fermentation medium in 500 mL Erlenmeyer flasks. The fermentation medium had the following composition:

|  | % By Wgt |
| --- | --- |
| Glucose | 0.5 |
| Lactose | 2.0 |
| Dextrin | 2.0 |
| Corn steep liquor | 1.0 |
| Pharmamedia | 1.5 |
| EBIOS powder* | 0.2 |
| $CaCO_3$ | 0.3 |
| Water | to 100 |

*Asahi Brewer Co., Ltd.

The pH of the medium was adjusted to pH 7.0 before autoclaving at 121° C. for 20 minutes.

The fermentation proceeded for 144 hours, with the same conditions of incubation as described above for the seed fermentation, and then harvested.

(B) Isolation of Hayumicin A and Hayumicin B

The fermentation broth (30 liters) obtained as above was stirred vigorously with n-butanol (12 liters) for one hour, after which the butanol layer was separated and concentrated in vacuo to dryness. The residue (25 g) was dissolved in 70% aqueous methanol (300 mL) and charged onto a column of Diaion HP-20 (Mitsubishi Kasei, 900 mL). After washing the column with 50% aqueous methanol (1.5 liters) and then with 80% aqueous methanol (1 liter), the column was developed with 90% aqueous acetone (2 liters) in order to elute the activity. The active fractions were pooled and concentrated in vacuo to yield a residue (2.7 g). The residue, dissolved in a solvent mixture of chloroform:methanol (10:1) was applied to a silica gel column (Silica Gel 60, Merck, 600 mL), which was then developed stepwise with chloroform-methanol (10:1), chloroform-methanol (4:1), methanol and then chloroform-methanol-water (4:7:2). Fractions (20 mL) were collected and tested by thin layer chromatography (Silica gel 60 $F_{254}$, Merck, $CHCl_3$-methanol, 4:1) and bioautography for antibiotic activity against *Micrococcus luteus* ATCC 9341. The active fractions that eluted with chloroform-methanol (10:1) were combined and concentrated in vacuo to give 617 mg of partially purified Hayumicin B. The active fractions that eluted with chloroform-methanol-water (4:7:2) yielded 63 mg of partially purified Hayumicin A.

A portion (90 mg) of the partially purified Hayumicin B preparation obtained above was dissolved in a solvent mixture of chloroform:methanol (10:1) and applied to a column of Sephadex LH-20 (350 mL). The column was developed with chloroform-methanol (1:1). Fractions containing a purple pigment were pooled and concentrated in vacuo, yielding pure Hayumicin B (52 mg).

The partially purified Hayumicin A (63 mg) obtained above was dissolved in the solvent mixture of chloroform:methanol (10:1) and charged onto a column of Sephadex LH-20 (350 mL). The column was eluted with chloroform-methanol (1:1). Fractions containing a purple pigment were pooled and concentrated in vacuo to give pure Hayumicin A (50 mg).

(C) Physico-chemical Properties of Hayumicin A and Hayumicin B

Both Hayumicin A and Hayumicin B components were isolated as purple amorphous powders, which were readily soluble in dimethylsulfoxide and pyridine, slightly soluble in chloroform and methanol and insoluble in n-hexane and water. Both gave positive responses to ferric chloride and anthrone reagents, and were negative in the Sakaguchi test. The molecular formula of Hayumicin A was found to be $C_{34}H_{34}O_{14}$ and that for Hayumicin B was found to be $C_{34}H_{35}NO_{13}$, based on high resolution FAB-MS spectrometry. The physico-chemical properties of these two antibiotic compounds are given in the following Table 4. The $^1H$ NMR spectra, the $^{13}C$ NMR and the IR spectra are shown in FIGS. 1 to 6, as described above. The structures of Hayumicin A and Hayumicin B were elucidated by analyses of the IR, UV and NMR spectral data, including 2 D NMR ($^1H$-$^1H$ COSY and NOESY, $^{13}C$-$^1H$ COSY, long range $^{13}C$-$^1H$ COSY and HMBC).

TABLE 4

Physico-chemical properties of Hayumicin A and Hayumicin B

|  | Hayumicin A | Hayumicin B |
| --- | --- | --- |
| Appearance | Purple powder | Purple powder |
| Melting point | 185–187° C. | 190–192° C. |
| Molecular formula | $C_{34}H_{34}O_{14}$ | $C_{34}H_{35}NO_{13}$ |
| Molecular weight | 666 | 665 |
| Positive FAB-MS (m/z) | 667 $(M + H)^+$ | 688 $(M + Na)^+$ |
| HRFAB-MS (m/z) |  |  |
| Obsd. | 667.2031 | 688.1998 |
| Calcd. | 667.2027 | 688.2006 |
| $UV\lambda_{max\ nm}^{(E^{1\%}_{1cm})}$ |  |  |
| in MEOH* | 238 (507) | 230 (575) |
|  | 259 (409) | 244 (sh, 500) |
|  | 288 (sh, 233) | 264 (466) |
|  | 316 (150) | 387 (82) |
|  | 385 (sh, 79) | 536 (206) |
|  | 546 (116) | 574 (218) |
| in 0.01N HCl-MeOH | 239 (522) | 232 (584) |
|  | 259 (410) | 244 (sh, 518) |
|  | 287 (238) | 264 (482) |
|  | 318 (174) | 388 (120) |
|  | 386 (sh, 78) | 544 (222) |
|  | 540 (111) | 580 (227) |
| in 0.01N NaOH-MeOH | 227 (499) | 238 (458) |
|  | 246 (sh, 451) | 269 (350) |
|  | 266 (429) | 364 (149) |

TABLE 4-continued

Physico-chemical properties of Hayumicin A and Hayumicin B

| | Hayumicin A | Hayumicin B |
|---|---|---|
| | 401 (86) | 684 (81) |
| | 560 (138) | |
| | 594 (sh, 124) | |
| IR ν max (KBr) cm$^{-1}$ | 3430, 1730, 1670, 1630, 1600, 1260, 1100–1000 | 3422, 1728, 1652, 1628, 1590, 1290, 1100–1000 |
| TLC, SiO$_2$, (CHCl$_3$-MeOH = 4:1) | R$_f$ 0.12 | R$_f$ 0.66 |
| HPLC (YMC-Pack A301-3, CH$_3$CN-0.15% KH$_2$PO$_4$ buffer, pH 3.5, 15–80% gradient) | R$_t$ 11.3 min. | R$_t$ 10.8 min. |

*MeOH = methanol

EXAMPLE 2

Biological Activity of Hayumicin A and Hayumicin B

The following methodology was used to determine the minimum inhibitory concentration (hereinafter referred to as the "MIC") of the compounds of this invention. The test organisms were grown in 20 mL of Antibiotic Assay Broth (Difco) by inoculating the broth (in tubes) with a loopful of the organism from a BHI (Difco) agar slant. The inoculated tubes were incubated at 37° C. for 18 to 24 hours. These cultures were assumed to contain 10$^9$ colony forming units (CFU) per mL. The cultures were diluted 1:100 to give a final inoculum level of 10$^7$ CFU per mL; dilutions were made with Yeast Beef Broth (Difco). The antibiotics Hayumicin A and Hayumicin B of the present invention were dissolved in suitable diluents at a concentration of 1000 μg/mL. Two-fold dilutions were made in Yeast Beef Broth (Difco), resulting in a range from 1000 μg/mL to 0.5 μg/mL. A 1.5 mL portion of each dilution was placed into individual petri dishes to which 13.5 mL of K-10 agar was added. The composition of K-10 agar is:

| | |
|---|---|
| Beef extract | 1.5 g |
| Yeast extract | 3.0 g |
| Peptone | 6.0 g |
| Dextrose | 1.0 g |
| Agar | 15.0 g |
| Distilled water | q.s. to 1 liter |

The medium was sterilized at 121° C. for 20 minutes prior to use.

The final drug concentration in agar of Hayumicin A or Hayumicin B ranged from 128 μg/mL to 0.05 μg/mL. Organism growth control plates containing agar only were prepared and inoculated before and after the test plates. The organisms were applied to the surface of each plate so that each contained a final inoculum of 10$^5$ CFU. The plates were incubated at 37° C. for 18 hours and the MICs determined. The MIC is the lowest concentration of compound inhibiting growth of the organism.

The results of the agar dilution assays were as indicated on the following Table 5.

TABLE 5

| | | MIC (μg/mL) | |
|---|---|---|---|
| Organism | A No.* | Hayumicin A | Hayumicin B |
| Streptococcus pneumoniae | 9585 | 16 | 8 |
| Streptococcus pyogenes | 9604 | 8 | 8 |
| Streptococcus agalactiae | 22567 | 8 | 8 |
| Staphylococcus aureus | 24227 | 128 | 128 |
| Staphylococcus aureus | 9537 | 64 | 64 |
| Staphylococcus aureus | 9606 | 128 | 128 |
| Micrococcus luteus | 9852 | 1 | 1 |
| Bacillus subtilis | 9506A | 32 | 4 |
| Escherichia coli | 22292 | 16 | 128 |
| Escherichia coli | 20697 | >128 | >128 |
| Escherichia coli | 28290 | >128 | >128 |
| Klebsiella pneumoniae | 9664 | >128 | >128 |
| Klebsiella oxytoca | 203454 | >128 | >128 |
| Proteus mirabilis | 9900 | >128 | >128 |
| Pseudomanas aeruginosa | 21508 | >128 | >128 |

*Stock Culture Collection Number of Bristol-Myers Squibb Co.

EXAMPLE 3

Preparation of Hayumicin C$_1$, Hayumicin C$_2$ and Hayumicin D (A) Extraction and Purification Fermentation broth (30 liters) obtained as in step (A) of Example 1 was stirred vigorously with n-butanol (12 liters) for one hour. The butanol extract was concentrated in vacuo to dryness and the residue (25 g) was dissolved in 70% aqueous methanol (300 ml). This mixture was charged on a column of Diaion HP-20 (Mitsubishi Kasei, 900 ml) which was washed with 50% aqueous methanol (1.5 liters) and 80% aqueous methanol (1 liter), and then developed with 90% aqueous acetone (2 liters) to elute the activity. Concentration of the active eluate yielded a crude solid mixture of Hayumicin compounds (2.7 g). The solid was applied on a silica gel column (Silica Gel 60, Merck, 600 ml) which was developed stepwisely with chloroform-methanol (10:1 and 4:1), methanol and chloroform-methanol-water (4:7:2). The eluate was collected in fractions (20 ml), and each fraction was monitored by the antibiotic activity using Micrococcus luteus ATCC 9341 as the test organism and TLC (Silica gel 60 F$_{254}$, Merck, CHCl$_3$-MeOH, 4:1). First active eluates and second active eluates obtained from a chloroform-methanol (10:1) elution were evaporated under reduced pressure to give a semi-pure solid of Hayumicin B (617 mg) and a crude solid mixture of Hayumicins C$_1$ and C$_2$ (117 mg), respectively. Third active fractions obtained from a chloroform-methanol (4:1) elution gave a crude solid of Hayumicin D (129 mg). Concentration of a chloroform-methanol-water (4:7:2) eluate afforded a semi-pure solid of Hayumicin A (63 mg).

(B) Isolation of Hayumicins C$_1$ and C$_2$

The crude solid mixture of Hayumicins C$_1$ and C$_2$ (117 mg) was dissolved in 2 ml of chloroform-methanol (20:1) and subjected to the silica gel (80 ml) column chromatography. The column was eluted with the same solvent to give a purified sample (27 mg), which was found to be a solid mixture of Hayumicins C$_1$ and C$_2$ by TLC and HPLC. Separation of Hayumicins C$_1$ and C$_2$ was conducted by preparative TLC (Merck, Silica Gel 60 F$_{254}$, thickness 0.25 mm, CHCl$_3$-MeOH, 10:1) to obtain purple powders of Hayumicins C$_1$ (10 mg) and C$_2$ (4 mg). These solids were purified separately by a Sephadex LH-20 column eluted with chloroform-methanol (1:9) to afford pure Hayumicin C$_1$ (8.5 mg) and pure Hayumicin C$_2$ (1.9 mg), respectively.

(C) Isolation of Hayumicin D

The crude solid of Hayumicin D (129 mg) was dissolved in 2 ml of chloroform-methanol (20:1) and applied to a silica gel column (70 ml). The column was developed with chloroform-methanol (9:1) to give a semi-pure solid of Hayumicin D (19 mg). This material was further purified by Sephadex LH-20 (330 ml) column chromatography eluted with chloroform-methanol (2:3). Appropriate fractions were pooled and concentrated in vacuo to obtain a purple powder which was rechromatographed on a column of Sephadex LH-20 (330 ml). The column was developed with chloroform-methanol (1:9), yielding a pure solid of Hayumicin D (2.4 mg).

Figure 7:
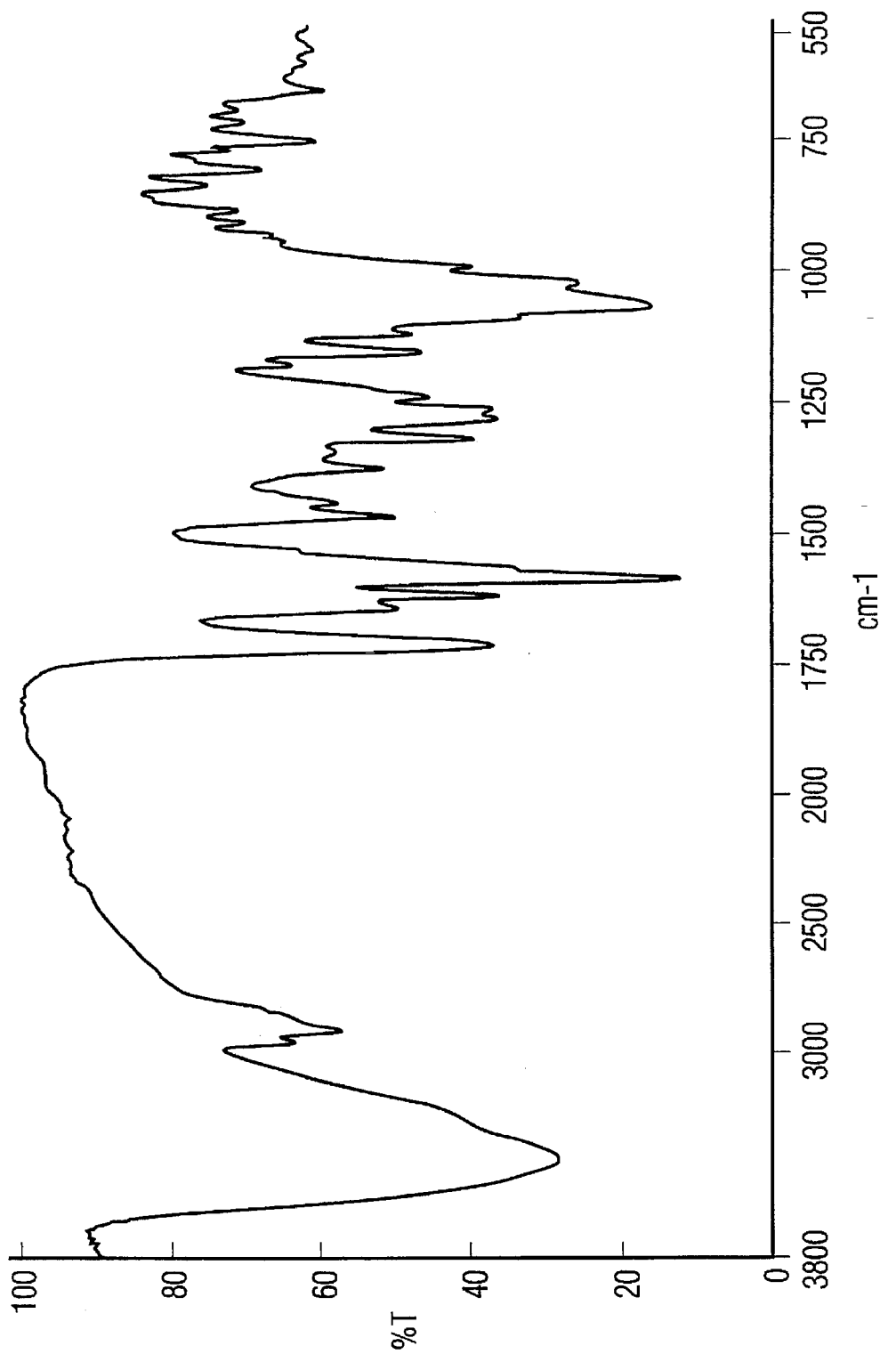
FIG. 7 shows the infrared (IR) spectrum of Hayumicin $C_1$ in KBr.
Figure 8:
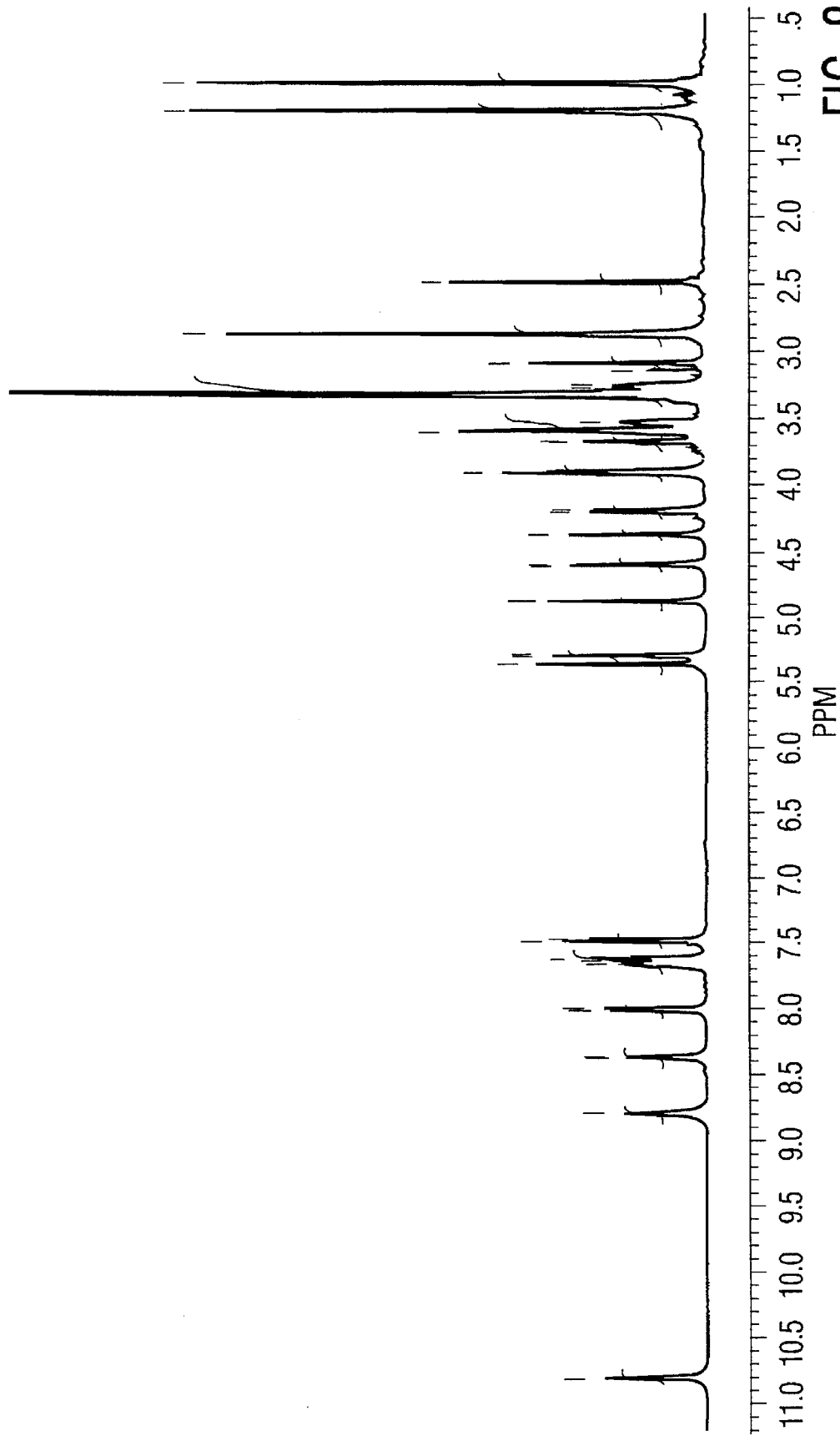
FIG. 8 shows the $^1$H NMR spectrum of Hayumicin $C_1$ in dimethylsulfoxide (DMSO-$d_6$), 500 MHz.
Figure 9:
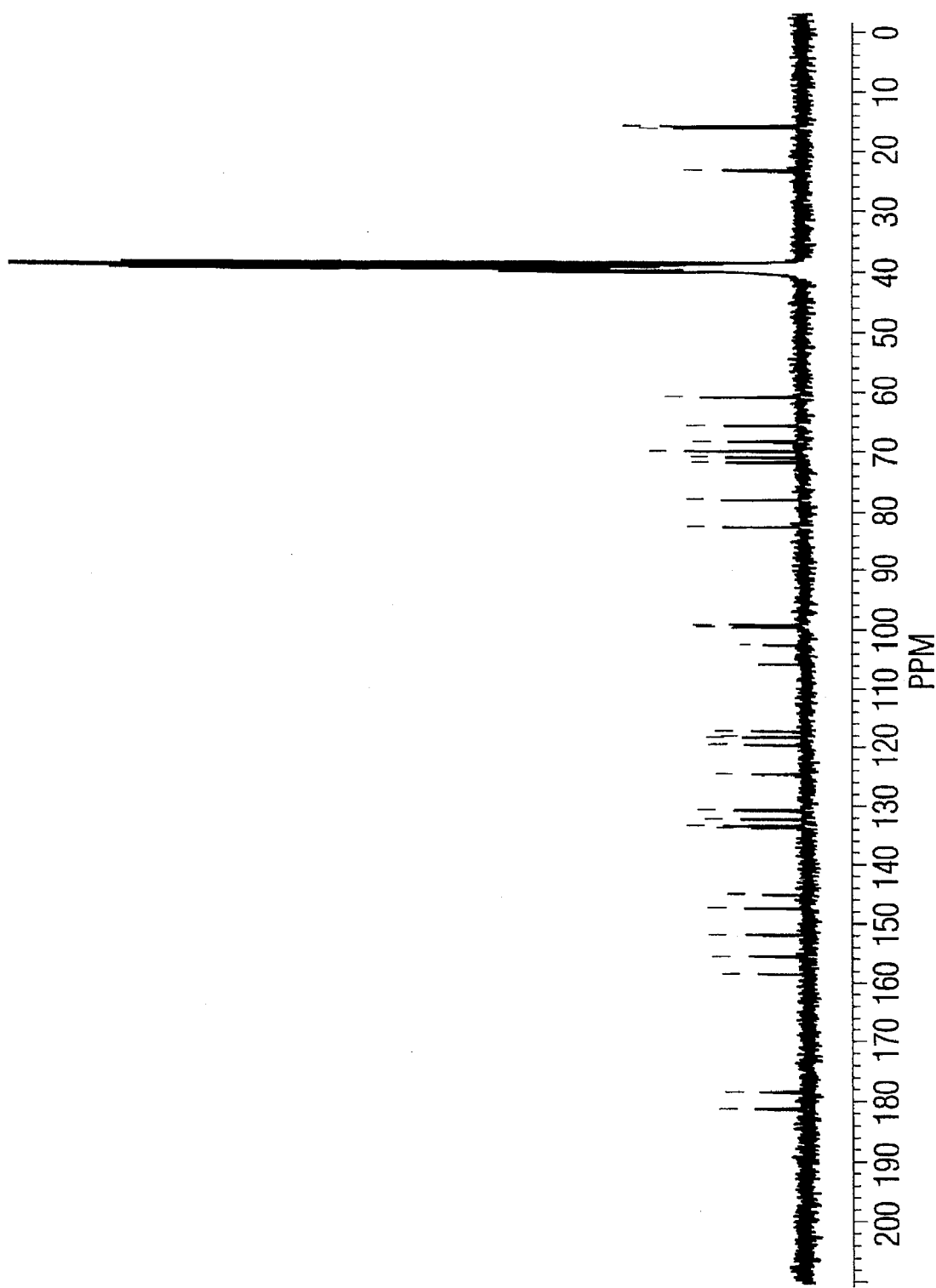
FIG. 9 shows the $^{13}$C NMR spectrum of Hayumicin $C_1$ in dimethylsulfoxide (DMSO-$d_6$), 125 MHz.
Figure 10:
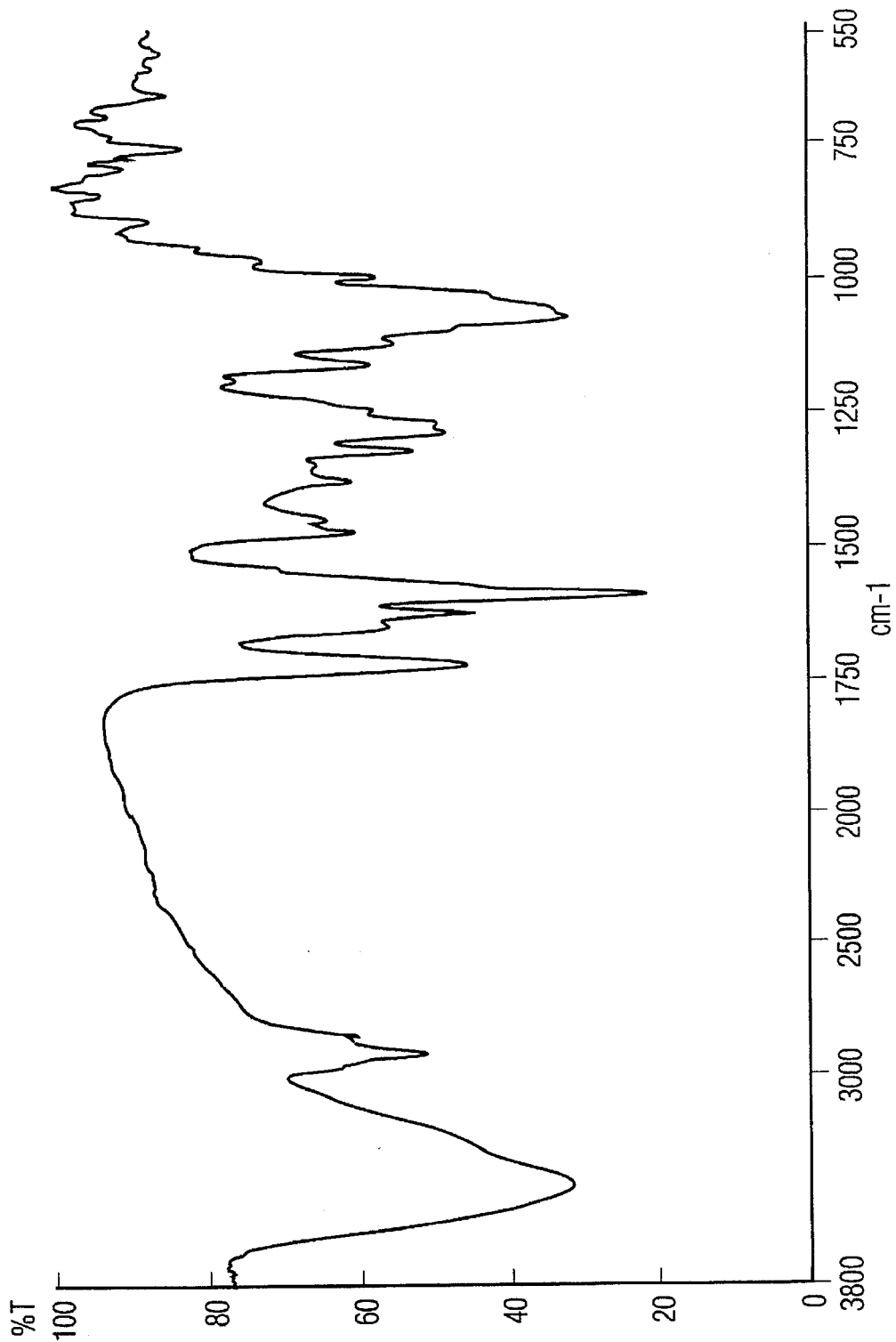
FIG. 10 shows the infrared (IR) spectrum of Hayumicin $C_2$ in KBr.
Figure 11:
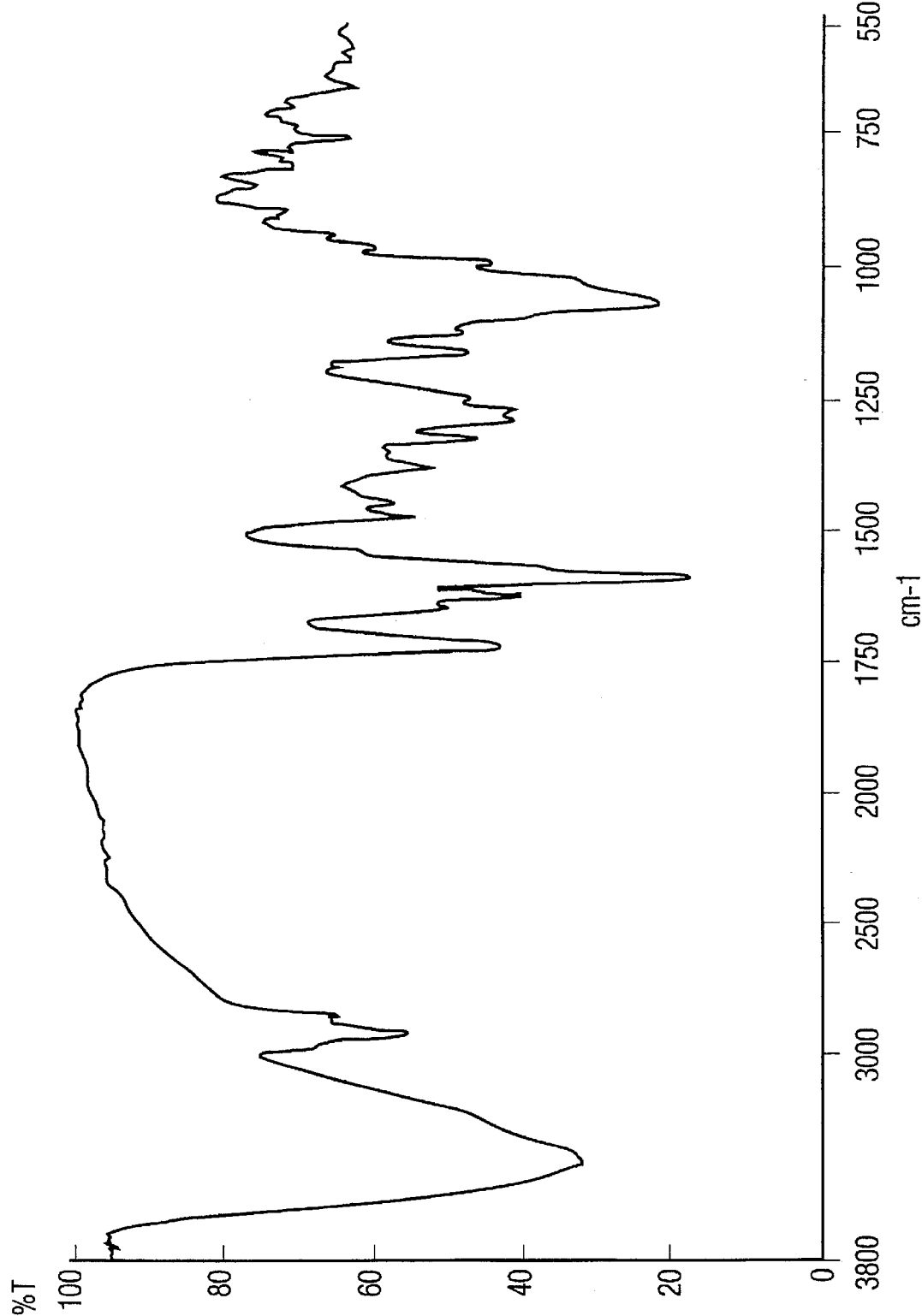
FIG. 11 shows the infrared (IR) spectrum of Hayumicin D in KBr.
Figure 12:
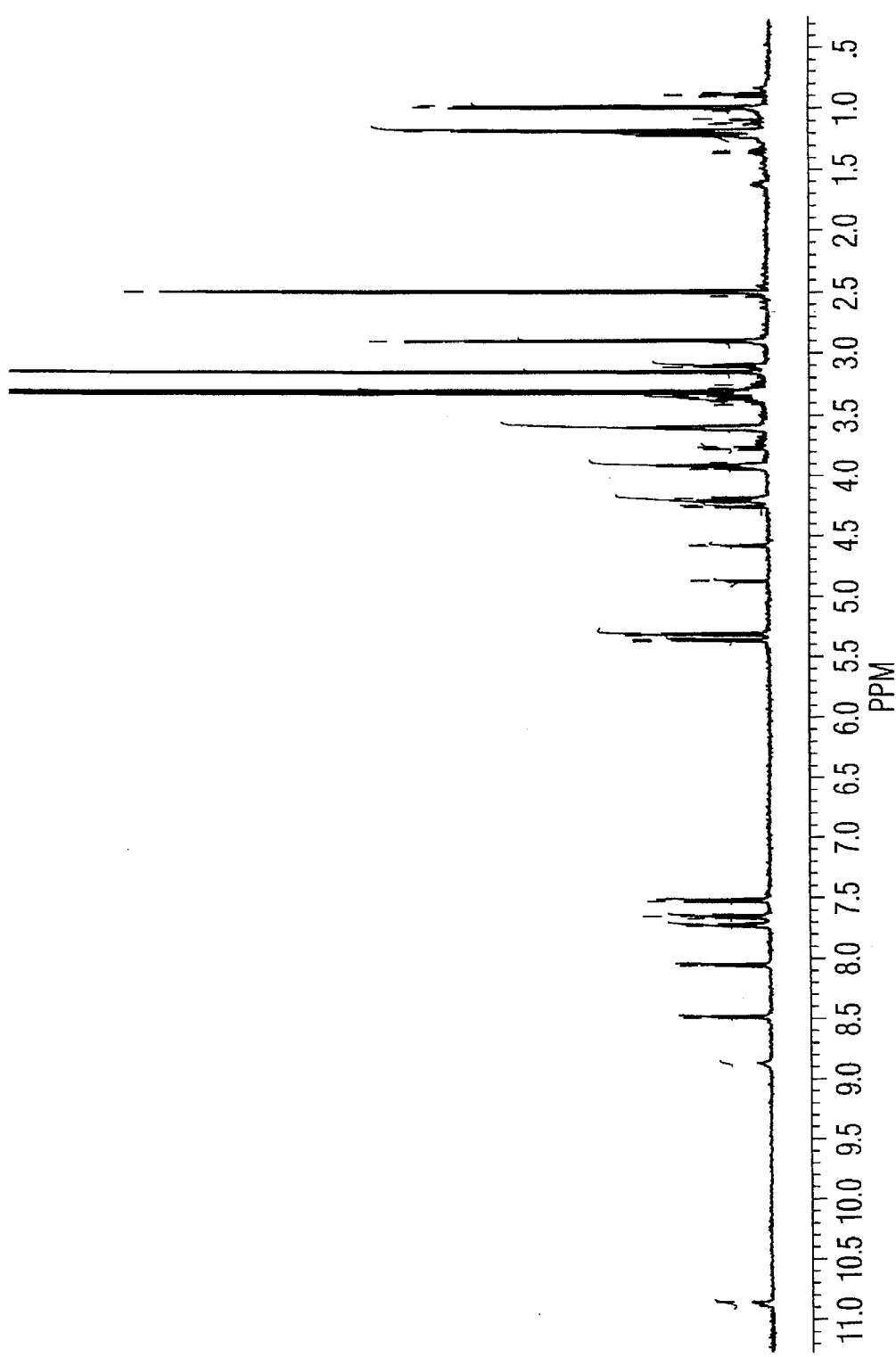
FIG. 12 shows the $^1$H NMR spectrum of Hayumicin $C_2$ in dimethylsulfoxide (DMSO-$d_6$), 500 MHz.
Figure 13:
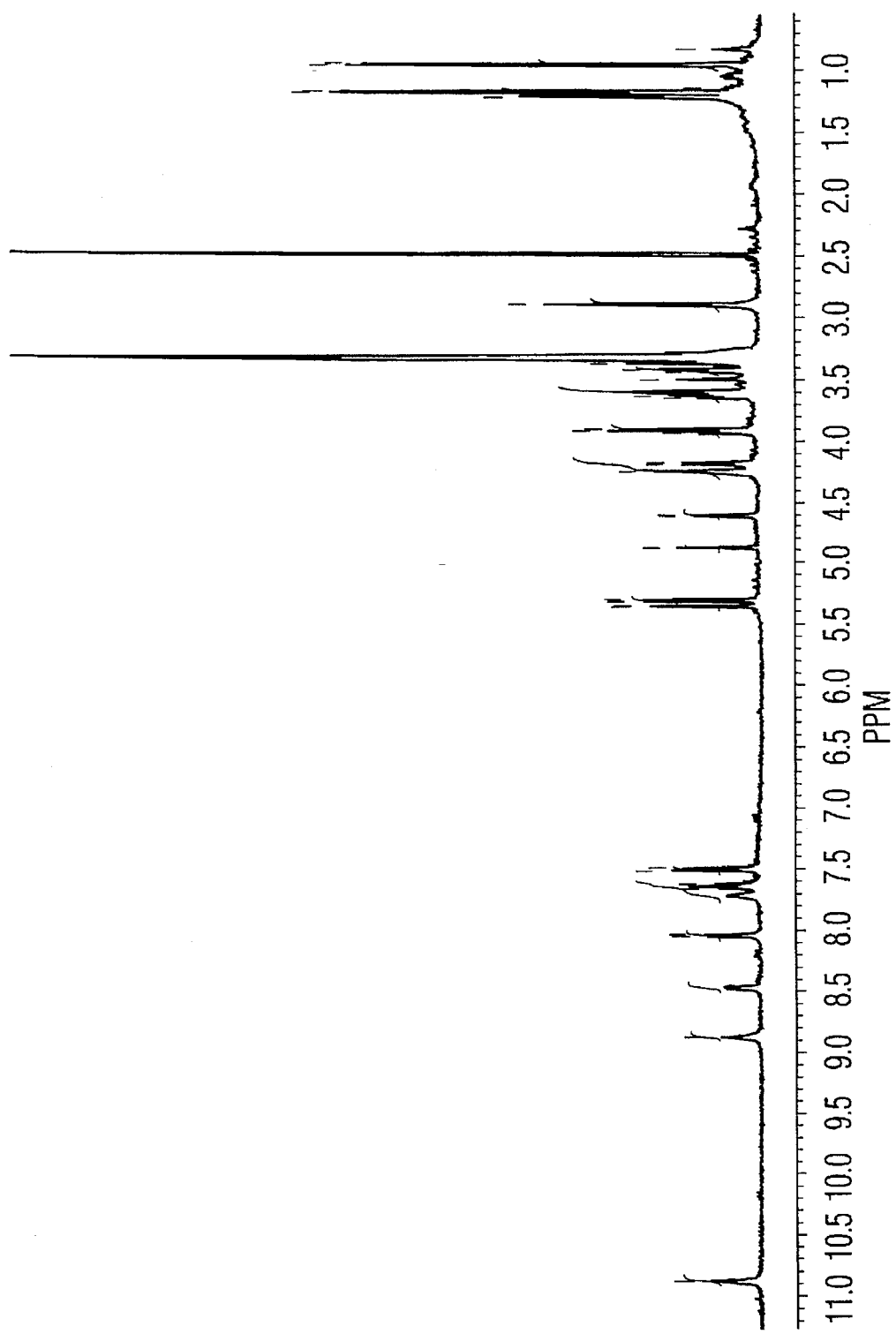
FIG. 13 shows the $^1$H NMR spectrum of Hayumicin D in dimethylsulfoxide (DMSO-$d_6$), 500 MHz.

(D) Physico-chemical Properties and Chemical Structures of Hayumicins C$_1$, C$_2$ and D Hayumicins C$_1$, C$_2$ and D were isolated as a purple amorphous powder. The compounds are soluble in dimethylsulfoxide and pyridine, slightly soluble in chloroform and methanol and practically insoluble in n-hexane, ether and water. They give a positive response to anthrone reagent, but are negative to Sakaguchi test. The molecular formulae of Hayumicins C$_1$, C$_2$ and D were determined to be C$_{33}$H$_{33}$NO$_{13}$, C$_{33}$H$_{33}$NO$_{13}$ and C$_{32}$H$_{31}$NO$_{13}$, respectively, based on the high-resolution FAB-MS spectral results. The physico-chemical data of Hayumicin C$_1$ are summarized in Table 6; the physico-chemical data of Hayumicin C$_2$ are summarized in Table 7; and the physico-chemical data of Hayumicin D are summarized in Table 8. The UV and IR spectra of Hayumicins C$_1$, C$_2$ and D are similar to each other. The IR, $^1$H NMR and $^{13}$C NMR spectra of Hayumicin C$_1$ are shown in FIGS. 7, 8 and 9, respectively. The IR spectra of Hayumicins C$_2$ and D are shown in FIGS. 10 and 11, respectively. The $^1$H NMR spectra of Hayumicins C$_2$ and D are shown in FIGS. 12 and 13, respectively. The structures of Hayumicins C$_1$, C$_2$ and D were elucidated on the basis of comparison studies of their $^1$H and $^{13}$C NMR spectra with those of Hayumicin B. They were found to be des-methyl congeners of Hayumicin B with one methyl missing in Hayumicins C$_1$ and C$_2$ and two methyls missing in Hayumicin D on their sugar moieties.

TABLE 6

Physico-chemical Properties of Hayumicin C$_1$

| | |
|---|---|
| Appearance | Purple Powder |
| Melting point (°C.) | 238–245 |
| Molecular formula | C$_{33}$H$_{33}$NO$_{13}$ |
| Molecular weight | 651 |
| FAB-MS (m/z) | 652 (M+H)$^+$ |
| HRFAB-MS (m/z) | |
| Obsd. | 652.2006 |
| Calcd. | 652.2031 |
| UV$\lambda_{max}^{nm}$ (E$_{1cm}^{1\%}$) in MeOH | 230(385), 242(sh, 337), 264(309), 388(77), 537(136), 575(147) |
| in 0.01N HCl-MeOH | 230(396), 243(sh, 346), 264(318), 388(75), 540(136), 576(144) |
| in 0.01N NaOH-MeOH | 242(279), 269(222), 364(92), 689(55) |
| IR v max$^{(KBr)}$ cm$^{-1}$ | 3416, 1724, 1652, 1626, 1590, 1100–1000 |
| TLC, SiO$_2$ (CHCl$_3$-MeOH = 4:1) | Rf 0.54 |
| HPLC | Rt 13.2 min. |

TABLE 6-continued

Physico-chemical Properties of Hayumicin C$_1$

| | |
|---|---|
| (YMC-Pack A301-3, CH$_3$CN-0.15% KH$_2$PO$_4$ buffer, pH 3.5, 15–50% gradient) | |

TABLE 7

Physico-chemical Properties of Hayumicin C$_2$

| | |
|---|---|
| Appearance | Purple Powder |
| Melting point (°C.) | 185–195 |
| Molecular formula | C$_{33}$H$_{33}$NO$_{13}$ |
| Molecular weight | 651 |
| FAB-MS (m/z) | 652 (M+H)$^+$ |
| HRFAB-MS (m/z) | |
| Obsd. | 652.2050 |
| Calcd. | 652.2031 |
| UV$\lambda_{max}^{nm}$(E$_{1cm}^{1\%}$) in MeOH | 230(287), 242(sh, 245), 264(224), 388(55), 537(100), 575(108) |
| IR v max$^{(KBr)}$ cm$^{-1}$ | 3420, 1724, 1652, 1626, 1590, 1100–1000 |
| TLC, SiO$_2$ (CHCl$_3$-MeOH = 4:1) | Rf 0.57 |
| HPLC (YMC-Pack A301-3, CH$_3$CN-0.15% KH$_2$PO$_4$ buffer, pH 3.5, 15–50% gradient) | Rt 12.8 min. |

TABLE 8

Physico-chemical Properties of Hayumicin D

| | |
|---|---|
| Appearance | Purple Powder |
| Melting point (°C.) | 236–243 |
| Molecular formula | C$_{32}$H$_{31}$NO$_{13}$ |
| Molecular weight | 637 |
| FAB-MS (m/z) | 660 (M+Na)$^+$ |
| HRFAB-MS (m/z) | |
| Obsd. | 660.1671 |
| Calcd. | 660.1603 |
| UV$\lambda$ max$^{nm}$ (E$_{1cm}^{1\%}$) in MeOH | 230(370), 244(sh, 317), 264(289), 388(65), 538(111), 575(119) |
| IR v max$^{(KBr)}$ cm$^{-1}$ | 3414, 1722, 1652, 1626, 1590, 1100–1000 |
| TLC, SiO$_2$ (CHCl$_3$-MeOH = 4:1) | Rf 0.26 |
| HPLC (YMC-Pack A301-3, CH$_3$CN-0.15% KH$_2$PO$_4$ buffer, pH 3.5, 15–50% gradient) | Rt 12.3 min. |

EXAMPLE 4

Preparation of Sodium Salt of Hayumicin A

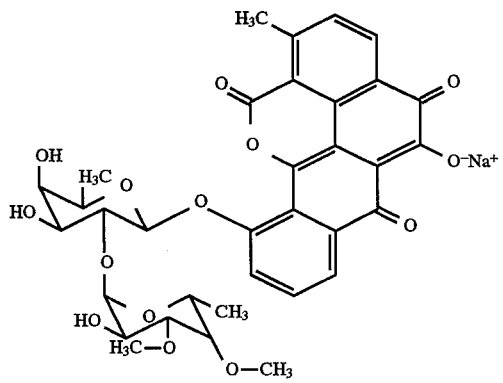

Hayumicin A (10 mg) is dissolved in 60% aqueous tert-butanol (10 ml) and adjusted to pH 7.5 with 1N NaOH. The solution is lyophilized to yield the title sodium salt of Hayumicin A (11 mg).

EXAMPLE 5

Preparation of Hydrochloride Salt of Hayumicin B

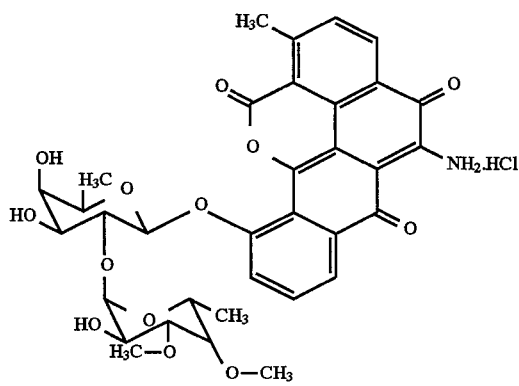

Hayumicin B (10 mg) is dissolved in 60% aqueous tert-butanol (10 ml) and adjusted to pH 2.0 with 1N HCl. The solution is lyophilized to yield the title hydrochloride salt of Hayumicin B (11 mg).

EXAMPLE 6

Preparation of Methyl Ether of Hayumicin A

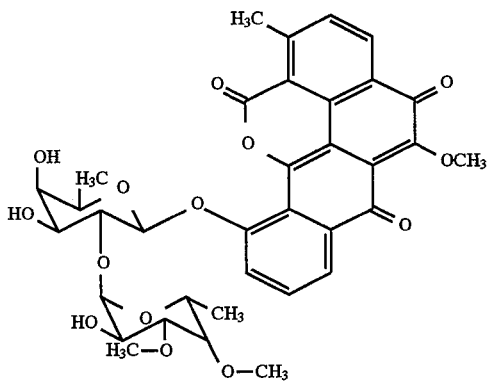

To a solution of Hayumicin A (13 mg) in methanol (20 ml) is added diazomethane in ether and the solution is kept standing for 1 hour. The solution is evaporated to dryness, which after purification by silica gel chromatography yields the title methyl ether of Hayumicin A (3 mg).

EXAMPLE 7

Preparation of Mono-N-acetyl, tri-O-acetyl Hayumicin B

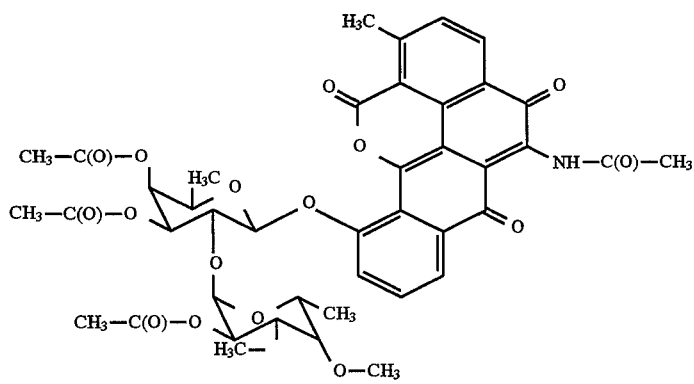

To a solution of Hayumicin B (3 mg) in methanol (5 ml) is added acetic anhydride (0.5 ml) and 4-dimethylaminopyridine (5 mg). The mixture is stirred overnight at room temperature. The reaction solution is concentrated to dryness, which after silica gel purification yields the title mono-N-acetyl, tri-O-acetyl derivative of Hayumicin B (3 mg).

EXAMPLE 8

Preparation of Benzoyl Ester of Hayumicin A

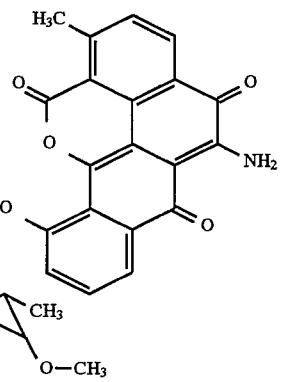

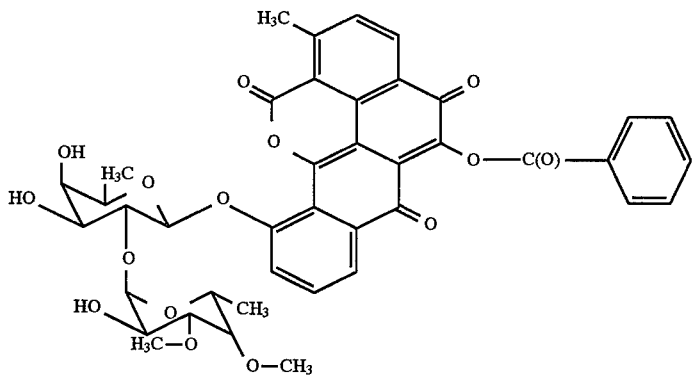

To a solution of Hayumicin A (5 mg) in tetrahydrofuran (7 ml) is added benzoyl chloride (0.5 ml) and triethylamine (0.1 ml). The solution is stirred overnight at room temperature. The reaction mixture is worked up, followed by purification with a silica gel column, affording the title benzoyl ester of Hayumicin A (2 mg).

What is claimed is:

1. A compound which is Hayumicin $C_1$, which compound has the following structure:

2. An antibacterial pharmaceutical composition, comprising a physiologically tolerated compound of claim 1, and a physiologically tolerated vehicle or diluent.

3. A composition for the inhibition of bacterial growth, comprising a compound of claim 1 in an amount effective therefor, and a vehicle or diluent.

4. An antitumor pharmaceutical composition, comprising a physiologically tolerated compound of claim 1, and a physiologically tolerated vehicle or diluent.

5. A compound of claim 1 which is substantially pure.

* * * * *